United States Patent [19]

Rogel et al.

[11] 4,219,774

[45] Aug. 26, 1980

[54] AUTOMATIC EDDY CURRENT SURFACE PROBE FOR FASTENER HOLES

[76] Inventors: Albert P. Rogel, 2655 Ellenbrook Dr., Rancho Cordova, Calif. 95670; Joseph J. Scalese, 5531 Laird Way, Loomis, Calif. 95650

[21] Appl. No.: 937,020

[22] Filed: Aug. 25, 1978

[51] Int. Cl.² ............................................. G01R 33/00
[52] U.S. Cl. .................................... 324/262; 324/228; 324/234; 324/238
[58] Field of Search ............... 324/226, 228, 233, 234, 324/235–240, 262; 408/150, 151

[56] References Cited

U.S. PATENT DOCUMENTS

| 3,109,139 | 10/1963 | Branher | 324/240 |
| 3,218,855 | 2/1973 | Rogel et al. | 324/234 |
| 3,831,084 | 8/1974 | Scalese et al. | 324/219 |
| 4,095,181 | 6/1978 | Harris et al. | 324/238 |

FOREIGN PATENT DOCUMENTS 296032   1/1971   U.S.S.R. .................................. 324/228

Primary Examiner—Rudolph V. Rolinec
Assistant Examiner—Walter E. Snow
Attorney, Agent, or Firm—Joseph E. Rusz; Henry S. Miller

[57] ABSTRACT

An eddy current flaw detector is held in a mounting block by a spring bias, the mounting block is selectively rotatable about a shank member for varying the radius of the detector as the shank rotates about a pivot point, turned by an electric drive mechanism.

4 Claims, 3 Drawing Figures

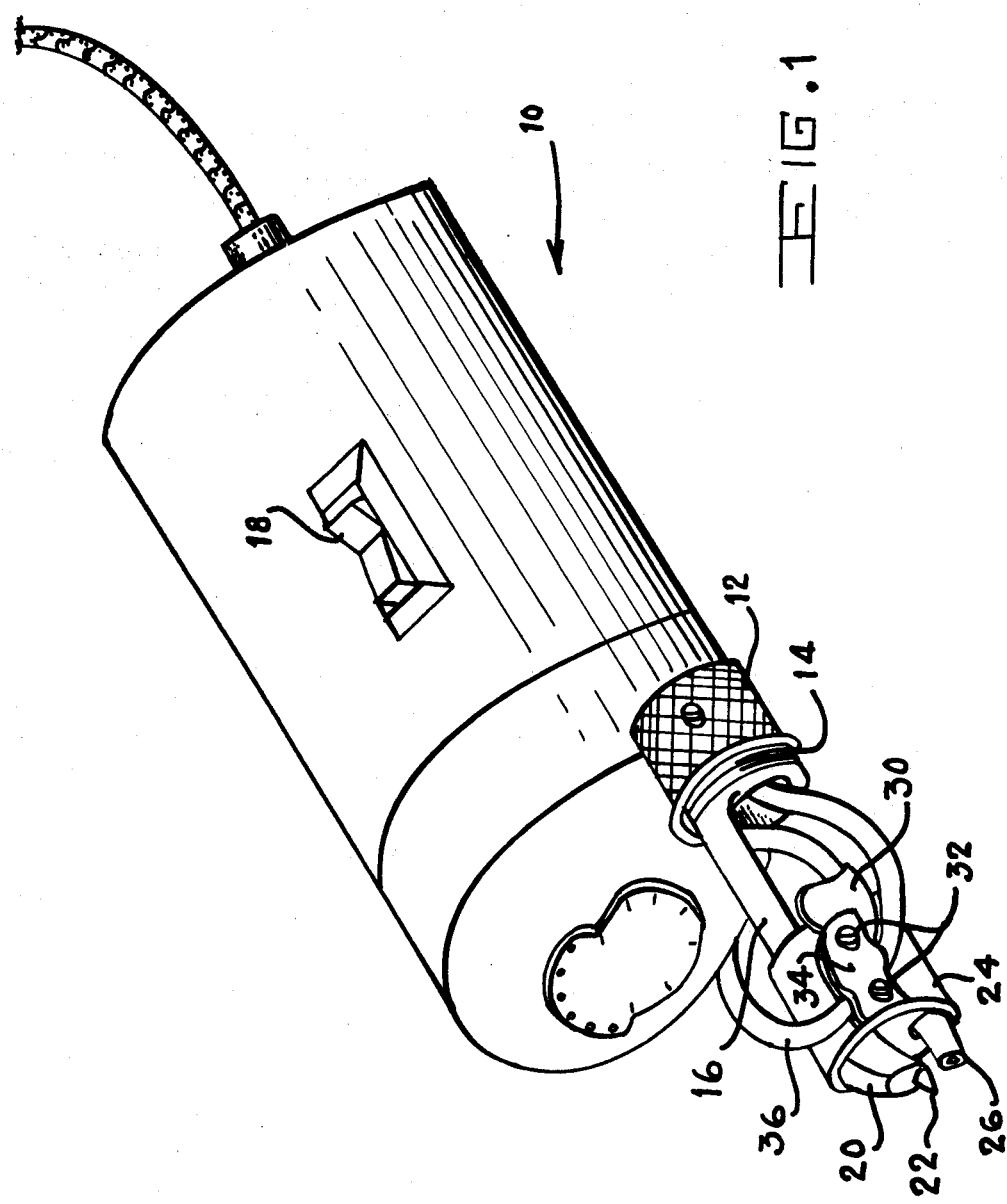

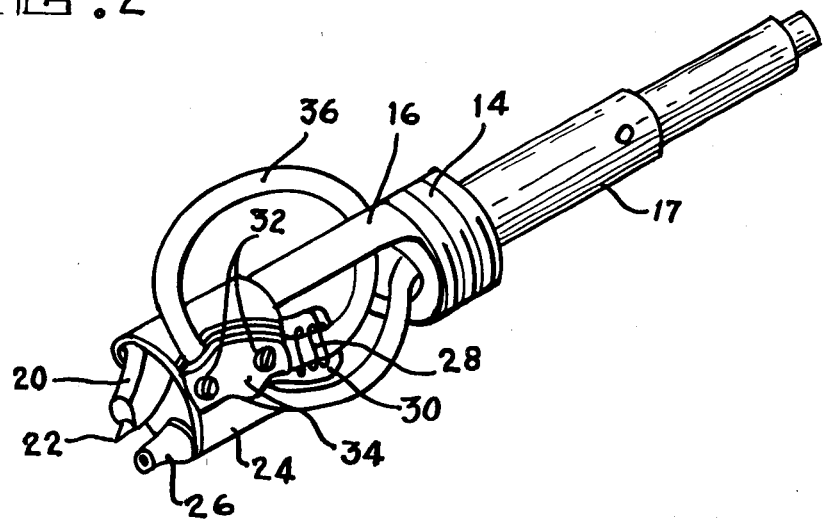
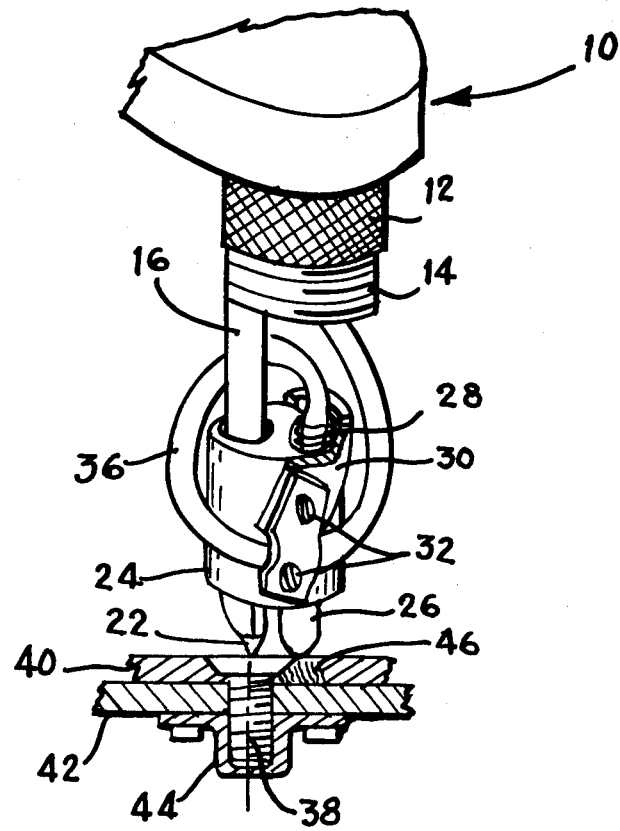

AUTOMATIC EDDY CURRENT SURFACE PROBE FOR FASTENER HOLES

STATEMENT OF GOVERNMENT INTEREST

The invention described herein may be manufactured and used by or for the Government for governmental purposes without the payment of any royalty thereon.

BACKGROUND OF THE INVENTION

This invention relates generally to non destructive flaw detection in metals and more particularly to such flaw detection in and around fasteners without the need to remove the fastener.

As a matter of routine safety inspection, aircraft and other vehicles and machines are inspected for fatigue and damage during periodic maintainence checks. Many systems of inspection are used including penetrating dyes, ultrasonics and magnetic field generator-detectors. Any particular system may have a particular type of test situation where it is more efficient then another systems. However, until now there has never been an acceptable system that could test fastener holes without first removing the fastener.

A fastener, whether it is a bolt, rivet or some other similar device has a head which covers an area on or near the surface of the material. This head has precluded non destructive testing for cracks or other fatigue or accidentally induced damage. In the past it was always necessary to remove the fastener.

The time and labor involved in removing a fastener increases the cost of inspection substantially. A way has been long sought to enable safe, accurate non destructive testing to take place in the case of fastener holes.

One prior art device suggests the use of the Hall Effect to measure the intensity of an induced magnetic flux directly. This technique requires two costly sensing elements along with a complex probe structure. Further, this type of system has shown to be less reliable and accurate then the eddy current floating probe proposed herein. Hall Effect type devices are sensitive to thickness of the structural member, localized variations in metallurgy, electrical or physical characteristics of the material, surface variations which affect the distances between the Hall devices and surface of the material being inspected, and temperature variations.

SUMMARY OF THE INVENTION

The invention involves an eddy current probe supported by a fixture adapted to fit an automatic motorized probe driving instrument.

In an earlier invention (U.S. Pat. No. 3,831,084 issued Aug. 20, 1974) an eddy current scanning device was disclosed which was adapted to be attached to the work piece and the probe could be made to follow a helical path into and out of an aperture. Alternatively, the probe could be set to rotate in a given plane.

This invention utilizes the drive mechanism of the aforemention invention set to drive the probe in a given plane. The mechanism is now hand held and not affixed to the work piece. A threaded extension from the drive spindle connects to a probe shank having an offset pivot at the distal end. Secured to the rotatable shank is the eddy current probe. The probe is so mounted as to be movable and spring biased along an axis parallel to the longitudinal axis of the shank. Due to the slip ring contacts in the drive assembly the probe is capable of continuous 360° rotation. Where the pivot point of the shank is offset, rotation of the probe about the shank will change the radius about which it rotates.

In operation the pivot point of the shank is placed over the center of the fastener. The radius is adjusted to the desired amount and the drive mechanism started. Since the probe is spring biased irregularities in the surface or minor variations in alignment of the probe will not effect the reading. The probe is connected to an analyzing device equipped with a chart recorder to provide a permanent record of each scan.

It is therefore an object of the invention to provide a new and improved automatic eddy current surface probe.

It is another object of the invention to provide a new and improved automatic eddy current surface probe that is less expensive than any similar known device.

It is a further object of the invention to provide a new and improved automatic eddy current surface probe that is more rugged and more reliable then any known prior art device.

It is still another object of the invention to provide a new and improved automatic eddy current surface probe that includes recorded results for analyzing and interpretation of small defects.

It is still a further object of the invention to provide a new and improved automatic eddy current probe that will scan subsurface as well as surface.

It is another object of the invention to provide a new and improved automatic eddy current probe that will scan a full, continuous 360° at a uniform speed.

It is another object of the invention to provide a new and improved automatic eddy current probe that is easily adjustable to different size fastener heads.

It is another object of the invention to provide a new and improved automatic eddy current surface probe that is lower in cost then any similar known device.

It is another object of the invention to provide a new and improved automatic eddy current probe that is uneffected by irregular surfaces.

It is another object of the invention to provide a new and improved automatic eddy current probe that will inspect narrow edge surfaces.

These and other advantages, features and objects of the invention will become more apparent from the following description taken in conjunction with the accompanying drawings.

DESCRIPTION OF THE DRAWING

FIG. 1 is a perspective view of the invention;

FIG. 2 is a perspective view of the shank and probe of the invention.

FIG. 3 is a side elevational view of the invention.

DESCRIPTION OF THE PREFERRED EMBODIMENT

Referring now to FIGS. 1 and 2 the drive mechanism for the probe assembly is shown generally at 10. This drive assembly is the same drive mechanism as is used in the flow detection system disclosed in U.S. Pat. No. 3,718,855 issued Feb. 27, 1973.

A threaded coupling 12 is adapted to engage the threaded portion (14) of shank 16, holding the shank securely and causing it to rotate when switch 18 activates the drive mechanism.

Shank 16 is offset from the centerline of the drive spindle 17. Hence, as the drive spindle rotates the path of travel of the shank would be a circle. The end of the shank is angulated inwardly at 20 and affixed to the end is a pivot point 22 which is along the center line axis of the drive spindle.

Attached to the shank is a mounting block 24. The block is rotatable around the shank and locked in a selected position by a set screw (not shown). The mounting block has an opening therein to receive an eddy current probe 26. The probe and opening have corresponding shoulders which limit the extent to which the probe may extend beyond the end of the mounting block. The eddy current probe is retained in mounting block 24 by a spring 28 which allows the probe to move back into the mounting block if rough or irregular surfaces are encountered. A spring retainer 30 is secured to the side of the mounting block by bolts 32 which also secure plate 34 holding probe-sensor wire 33.

It should be noted that by rotating mounting block 24 around shank 16 the radius of between the probe 26 and the pivot point 22 will increase or decrease. Hence, the invention is readily adaptable to be used with fasteners of varying size. It should also be noted that the type and style of pivot point may be changed depending uon the nature of the work piece to be tested.

Concerning FIG. 3, the probe is shown in operation with pivot point 22 inserted into the head of a counter sunk fastener 38. The example illustrates a typical aircraft wing skin fastener with the wing skin at 40 a fitting 42 below the skin and a nut plate 44 adjacent to the fitting. It can be clearly seen that the probe 26 is run along the edge of fastener 38 and the eddy currents, shown by lines 46, move inwardly toward the fastener to examine under the fastener head.

Spring retainer 30 is seen in this figure, as a portion is cut away in other figures. The retainer partially surrounds lead 36 and holds spring 28 in position. When nuts 32 are removed the retainer is free, and once removed, pressure will be removed from the spring and the probe lifted from the opening in the mounting block. Due to the slip ring arrangement in the drive mechanism the probe is continuously rotatable and any number of recordings may be derived from the same fastener.

In another application the invention has been shown to provide excellent test results when inspecting small valve forgings. With the insertion of a fixture into the threaded aperture of the valve, the probe is adjusted to ride along the exposed edge of valve and a rapid, accurate inspection is made of the valve housing and threads.

It should be understood of course that the foregoing disclosure relates to only a preferred embodiment of the invention and that numerous modifications or alterations may be made therein without departing from the spirit and scope of the invention as set forth in the appended claims.

We claim:

1. An automatic eddy current surface probe adapted for use with a motorized probe driving means including a rotatable drive spindle comprising: an elongated shank means having a threaded portion at one end adapted to engage the rotatable drive spindle and having a pivot point at the other end; a mounting block having a first aperture therethrough for receiving said shank means, and a second cylindrically shaped aperture therein, parallel to and spaced from said first aperture; an eddy current probe mounted in said second aperture, for movement with respect to the mounting block and extending beyond the mounting block parallel to said pivot point.

2. An automatic eddy current surface probe according to claim 1 including, a spring means and spring retaining means for allowing biased movement of said probe relative to the mounting block.

3. An automatic eddy current surface probe according to claim 1 wherein said elongated shank means is connected to a point on the perimeter of the spindle means at one end and has an angulaton at the other end to cause the pivot point to coincide with the centerline of the spindle means.

4. An eddy current surface probe according to claim 3 where said first aperture is offset from the centerline of the spindle whereby rotation of the mounting block about the shank will vary the radius of the eddy current probe about the pivot point.

* * * * *